United States Patent
Schmidt (10) Patent No.: US 9,969,685 B2
(45) Date of Patent: May 15, 2018

(54) ENANTIOSELECTIVE SYNTHESIS OF PYRROLOINDOLE COMPOUNDS

(71) Applicant: BRISTOL-MYERS SQUIBB COMPANY, Princeton, NJ (US)

(72) Inventor: Michael Anthony Schmidt, Perth Amboy, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days. days.

(21) Appl. No.: 15/718,453

(22) Filed: Sep. 28, 2017

(65) Prior Publication Data
US 2018/0086701 A1 Mar. 29, 2018

Related U.S. Application Data

(60) Provisional application No. 62/400,766, filed on Sep. 28, 2016.

(51) Int. Cl.
C07D 209/10 (2006.01)
C07D 209/12 (2006.01)
C07F 7/18 (2006.01)

(52) U.S. Cl.
CPC ......... *C07D 209/10* (2013.01); *C07D 209/12* (2013.01); *C07F 7/1852* (2013.01)

(58) Field of Classification Search
CPC ............... C07D 209/10; C07D 209/12
See application file for complete search history.

(56) References Cited

U.S. PATENT DOCUMENTS

| 6,251,933 B1 * | 6/2001 | Denny | C07D 209/10 514/414 |
|---|---|---|---|
| 6,281,354 B1 | 8/2001 | Boger | |
| 8,461,117 B2 | 6/2013 | Sufi et al. | |
| 8,852,599 B2 | 10/2014 | Zhang et al. | |

FOREIGN PATENT DOCUMENTS

WO WO 2003/101962 A1 12/2003

OTHER PUBLICATIONS

Babu, et al., "Novel Synthesis of 2-Aryl and 2,3-Disubstituted Indoles by Modified Double Elimination Protocol," *Organic Letters*, vol. 07, No. 21, pp. 4641-4643, 2005.
Boger, et al., "CC-1065 and the Duocarmycins: Synthetic Studies," *Chem. Rev.*, vol. 97, pp. 787-828, 1997.
Boger, et al., "Total Synthesis of (+) CC-1065 and ent -(−)-CC-1065," *Jam Chem. Soc.*, vol. 110, pp. 1321-1323, 1988.
Boger, et al., "Total Synthesis and Preliminary Evaluation of (+)-and ent-(−)-Duocarmycin SA," *Jam Chem. Soc.*, vol. 115, pp. 9025-9036, 1993.
Boger, et al., "Reversed and Sandwiched Analogs of Duocarmycin SA: Establishment of the Origin of the Sequence-Selective Alkylation of DNA and New Insights into the Source of Catalysis," *J. Am. Chem. Soc.*, vol. 119, pp. 4987-4998, 1997.
Boger, et al., "1,2,8,8a-Tettrahydrocyclopropal[c] Pyrrolo[3,2-e] . . . ," *J. Org. Chem*, vol. 65, pp. 4101-4111, 2000.
Boger, et al., "Cc-1065 and the Duocarmycins: Unraveling the Keys to a New Class of Naturally Derived DNA Alkylating Agents," *Proc. Nat. Academy Sci.*, vol. 92, pp. 3642-3649, 1995.
Boyle, et al., Synthesis and Evaluation of Duocarmycin SA Analogs Incorporating the Methyl 1,2,8,8a-Tetrahydrocyclopropa[c] Oxazolo . . . , *Bioorganic & Medicinal Chemistry Letters.*, vol. 20, pp. 1854-1857, 2010.
Choi, et al., "Efficient Synthesis of Achiral seco-CI Subunit of Duocarmycin Pharmacophore," *Bull. Korean Chem. Soc.*, vol. 30, No. 11, pp. 2815-2818, 2009.
Fukuda, et al., "Synthesis and Antitumor Activity of Novel Cyclopropapyrrolindole (CPI) Derivatives Bearing Methoxycarbonyl and Trifluoromethyl Groups," *Bioorganic Medicinal Chemistry Letters*, vol. 7, No. 13, pp. 1683-1688, 1997.
Fukuda, et al., "Novel Syntheses of Optically Active CC-1065, U-73,975(Adozelesin), U-90,244(Carzelesin) . . . ," *Heterocycles*, vol. 45, No. 12, pp. 2303-2308, 1997.
Fukuda, et al., "Synthetic Studies on Duocarmycin.1. Total Synthesis of dl-Duocarmycin A and its 2-Epimer," *Tetrahedron*, vol. 50, No. 9, pp. 2793-2808, 1994.
Fukuda, et al., "A Novel Synthesis of (+)-Duocarmycin SA," *Tetrahedron Letters*, vol. 38, No. 41, pp. 7207-7208, 1997.
Fukuyama, et al., "Total Synthesis of the Duocarmycins," *J. Am. Chem. Soc.*, vol. 125, pp. 6630-6631, 2003.
Hiroya, et al., "New Synthetic Method for Indole-2-Carboxylate and Its Application to the Total Synthesis of Duocarmycin SA," *Organic Letters*, vol. 6, No. 17, pp. 2953-2956, 2004.
Hurley, et al., "Reaction of the Antitumor Antbiotic Cc-1065 with DNA: Sturcture of a DNA Adduct with DNA Sequence Specificity," *Science*, vol. 226, pp. 843-844, 1984.

(Continued)

Primary Examiner — Laura L. Stockton
(74) Attorney, Agent, or Firm — Yuan Chao (57) ABSTRACT

Compounds according to formula (I) or (II), wherein $R^1$, $R^2$, and $R^3$ are as defined in the specification, are versatile intermediates for the synthesis of DNA minor groove binder-alkylators having a cyclopropapyrroloindole (CPI) or seco-CPI alkylating subunit.

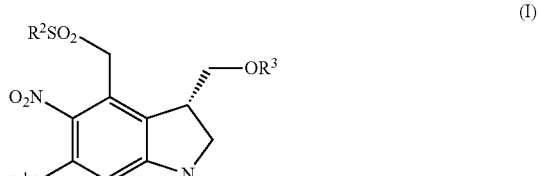

(I)

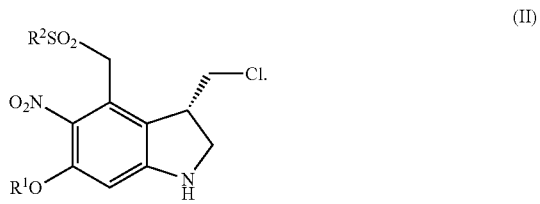

(II)

9 Claims, 3 Drawing Sheets (56) References Cited

OTHER PUBLICATIONS

Kinugawa, et al., "Practical Synthesis of the High-Quality Antitumor Agent KW-2189 from Duocarmycin B2 Using a Facile One-Pot Synthesis of an Intermediate," *Organic Process Research & Development*, vol. 2, pp. 344-350, 1998.

Kobayashi, et al., "Characteristics of Antitumor Activiy of KW-2189, a Novel Water-Soluble Derivative of Duocarmycin, Against Murine and Human Tumors," *Cancer Research*, vol. 54, pp. 2404-2410, 1994.

Kraus, et al., "Regioselective Diels-Alder Reactions. A Synthesis of the Left-Hand Portion of CC-1065," *J. Org. Chem.* vol. 50, 1985, pp. 283-284.

Kuwano, et al., "Highly Enantioselective Synthesis of Chiral 3-Substitued Indolins by Catalytic Asymmetric Hydrogenation of Indoles," *Organic Letters*, vol. 6, No. 13, pp. 2213-2215, 2004.

Lajiness, et al., "Design, Synthesis, and Evaluation of Duocarmycin o-Amino Phenol Prodrugs Subject to Tunable Reductive Activation," *Journal of Medicinal Chemistry*, vol. 53, pp. 7731-7738, 2010.

Li, et al., "Cytotoxicity and Antitumor Activity of Carzelesin, a Prodrug Cyclopropylprroloindole Analogue," *Cancer Research*, vol. 52, pp. 4904-4913, 1992.

Muratake, et al., "Total Synthesis of Natural (+)-Duocarmycin SA," *Chem. Pharm. Bull*, vol. 43, No. 6, pp. 1064-1066, 1995.

Murtake, et al., "Synthesis of Duocarmycin SA by Way of Methyl 4-(Methoxycarbonyl) . . . ," *Cham. Pharm. Bull*, vol. 46. No. 3,, pp. 400-412, 1998.

Muratake, et al., "Preparation of Alkyl-Substituted Indoles in the Benzene Portion. Part 15. Asymmetric Synthesis of . . . ," *Chem. Pharm. Bull*, vol. 46, No. 4, pp. 559-571, 1998.

Muratake, et al., "Preparation of Benzens, Furan, and Thiophene Analogs of Duocarmycin SA Employing a Newly-Devised Phenol-Forming Reaction," *Chem. Pharm. Bull*, vol. 48, No. 10, pp. 1558-1566, 2000.

Muratake, et al., "Total Synthesis of an Antitumor Antibiotic, (+)-Duocarmycin SA," *Tetrahedron Letters*, vol. 35, No. 16, pp. 2573-2576, 1994.

Sakamoto, et al., "Concise Synthesis of Cc-1065/Duocarmycin Pharmacophore Using the Intramolecular Heck Reaction," *J. Chem. Soc.*, pp. 1941-1942, 1993.

Tichenor, et al., "Systematic Exploration of the Structural Features of Yatakemycin Impacting DNA Alkylation and Biological Activity," *J. Am. Chem. Soc.*, vol. 129, pp. 10858-10869, 2007.

Tichenor, et al., "Asymmetric Total Synthesis of (+)-and ent-(−)-Yatakemycin and Duyocarmycin SA: . . . ," *J. Am. Chem. Soc.*, vol. 128, pp. 15683-15696, 2006.

Tietze, et al., "Highly Selective Glycosylated Prodrugs of Cytostatic CC-1065 Analogues for Antibody-Directed Enzyme Tumor Therapy," *ChemBioChem..*, vol. 2, pp. 758-765, 2001.

International Search Report and Written Opinion, for PCT Application No. PCT/US2017/053591, dated Jan. 2, 2018.

\* cited by examiner

ENANTIOSELECTIVE SYNTHESIS OF PYRROLOINDOLE COMPOUNDS

CROSS-REFERENCE TO RELATED APPLICATIONS

This application claims the benefit under 35 U.S.C. § 119(e) of U.S. Provisional Application Ser. No. 62/400,766, filed Sep. 28, 2016; the disclosure of which is incorporated herein by reference.

BACKGROUND OF THE INVENTION

1. Field of the Invention

This invention relates to the enantioselective synthesis of pyrroloindole compounds that are useful as intermediates for the synthesis DNA minor groove binder alkylators.

2. Description of Related Art

Double helical DNA has two longitudinal spiral grooves running along its exterior, much like the stripes on a barbershop pole. The two grooves are not identical: one, called the major groove, is much wider than the other, called the minor groove.

The width of the minor groove is approximately equal to the thickness of a benzene ring. Many biologically active DNA-binding molecules are substantially planar polyaromatic molecules having an arcuate footprint, such shape enabling them to fit snugly in the minor groove. One class of these molecules not only bind to DNA, but also alkylate it and are referred to as DNA minor groove binder-alkylators ("MGBAs").

An MGBA subclass is represented by the natural products CC-1065, duocarmycin SA, and yatakemycin (Boger and Johnson 1995; Tichenor et al. 2007). (Full citations for the documents cited herein by first author or inventor and year are listed at the end of this specification in the REFERENCES subsection.) They comprise an alkylating subunit and one or more binding subunits, the latter contributing to binding to DNA but being chemically unreactive towards it. In CC-1065 and duocarmycin SA, the alkylating subunit is at one end of the molecule and the binding subunit(s) are at the other end. In yatakemycin, the alkylating subunit is flanked by binding subunits. Consonant with the overall MGBA architecture, the alkylating and binding subunits themselves are polyaromatic and substantially planar. As the alkylating subunit has a cyclopropapyrroloindole ("CPI") core structure, MGBAs in this subclass are eponymously referred to as CPI compounds.

Duocarmycin SA

Yatakemycin

Upon binding to DNA, the CPI cyclopropyl ring is activated and alkylates DNA at an adenine N3 nitrogen (Hurley et al. 1984). One theory proposed to explain the activation is that binding introduces further conformational strain into the already-strained cyclopropyl ring, increasing its reactivity (Boger 2001; Boger et al. 1997b; Tichenor et al. 1997).

-continued

Seco-CPI compounds are variants of CPI compounds in which the cyclopropyl ring has been opened and replaced with a halomethyl group. While seco-CPI compounds themselves do not alkylate DNA, they are readily convertible in vitro or in vivo to CPI compounds and their biological activity is essentially the same as the latter's (Li et al. 2012). Thus, seco-CPI compounds are of interest as synthetically convenient functional equivalents of CPI compounds or as intermediates for their synthesis (Boger et al. 2000).

seco-CPI (Hal = Cl, Br) → CPI

An advantage of a seco-CPI compound is that it can be prodrugged to control conversion to the CPI form. Attaching a prodrugging group PD to the phenolic hydroxyl group prevents conversion to the CPI form unless PD is cleaved off first. PD can be chosen such that it is cleaved by an agent found at or near the site of intended biological action, such as a tumor, to reduce the risk of systemic toxicity. PD preferably is an enzymatically cleavable group, such as a carbamate, phosphate, glycoside, or glucuronide, which are cleavable by carboxyesterase, phosphatase, glycosidase, or glucuronidase, respectively. See, e.g., Kobayashi et al. 1994; Lajiness et al. 2010; Sufi et al. 2013; Tietze et al. 2001; Zhang et al. 2014.

CPI and seco-CPI compounds are potent cytotoxins, making them attractive candidates as anti-cancer agents. Substantial research efforts have been dedicated to synthesizing and evaluating their analogs for such use. A key challenge in the synthesis of CPI and seco-CPI compounds is the alkylating subunit, with its tricyclic structure and, in the case of CPI compounds, an additional fused cyclopropyl ring. Numerous disclosures relating to CPI and seco-CPI synthesis exist, including Boger et al. 1988, 1993, 1997a, and 2000; Boyle et al. 2010; Choi et al. 2009; Fukuda et al. 1994, 1997a, 1997b, and 1997c; Hiroya et al. 2004; Kinugawa et al. 1998; Kraus et al. 1985; Kuwano et al. 2004; Muratake et al. 1994, 1995, 1998a, 1998b, and 2000; Sakamoto et al. 1993; Tichenor et al. 2006; and Yamada et al. 2003.

BRIEF SUMMARY OF THE INVENTION

The present invention provides compounds that are versatile intermediates for the synthesis of CPI and seco-CPI compounds.

In one aspect, this invention provides a compound having a structure according to formula (I)

wherein $R^1$ is $CH_2$(phenyl) wherein the phenyl group is optionally substituted with one or more of Br, Cl, F, $C_1$-$C_3$ alkyl, $O(C_1$-$C_3$ alkyl), CN, $NH_2$, $NH(C_1$-$C_3)$alkyl, $N(C_1$-$C_3$ alkyl)$_2$, or $CF_3$; $CH_2$(naphthyl) wherein the naphthyl group is optionally substituted with one or more of Br, Cl, F, $C_1$-$C_3$ alkyl, $O(C_1$-$C_3$ alkyl), CN, $NH_2$, $NH(C_1$-$C_3)$ alkyl, $N(C_1$-$C_3$ alkyl)$_2$, or $CF_3$; trimethyl silyl (TMS); triethyl silyl (TES); triisopropyl silyl (TIPS); t-butyldiphenyl silyl (TBDPS); triphenylsilyl (TPS); or t-butyldimethyl silyl (TBS or TBDMS);

$R^2$ is an aromatic group selected from phenyl, naphthyl, pyridyl, pyrimidinyl, imidazolyl, and pyrazolyl, the aromatic group being optionally substituted with one or more of Br, Cl, F, $C_1$-$C_3$ alkyl, $O(C_1$-$C_3$ alkyl), CN, $NH_2$, $NH(C_1$-$C_3)$alkyl, $N(C_1$-$C_3$ alkyl)$_2$, or $CF_3$; and Prodrugged seco-CPI → seco-CPI → CPI $R^3$ is trimethyl silyl (TMS), triethyl silyl (TES), triisopropyl silyl (TIPS), t-butyldiphenyl silyl (TBDPS), triphenylsilyl (TPS), or t-butyldimethyl silyl (TBS or TBDMS);

or a salt thereof.

In another aspect, this invention provides a compound having a structure according to formula (II):

(II)

wherein $R^1$ and $R^2$ are as defined in respect of formula (I), or a salt thereof.

Compounds according to formula (I) and (II) are useful as precursors for the synthesis of CPI and seco-CPI compounds, as described in this application.

DETAILED DESCRIPTION OF THE INVENTION

In formulae (I) or (II), $R^1$ preferably is benzyl ($CH_2C_6H_5$, also referred to as Bn).

In formulae (I) or (II), $R^2$ preferably is phenyl ($C_6H_5$).

In formula (I), $R^3$ preferably is t-butydimethylsilyl (also referred to as TBS).

A preferred embodiment of compounds to formula (I) has a structure according to formula (Ia), that is, where $R^1$ is benzyl, $R^2$ is phenyl, and $R^3$ is t-butydimethylsilyl:

(Ia)

A preferred embodiment of compounds to formula (II) has a structure according to formula (IIa), that is, where $R^1$ is benzyl and $R^2$ is phenyl:

(IIa)

EXAMPLES

The practice of this invention can be further understood by reference to the following examples, which are provided by way of illustration and not of limitation.

Figure 1:
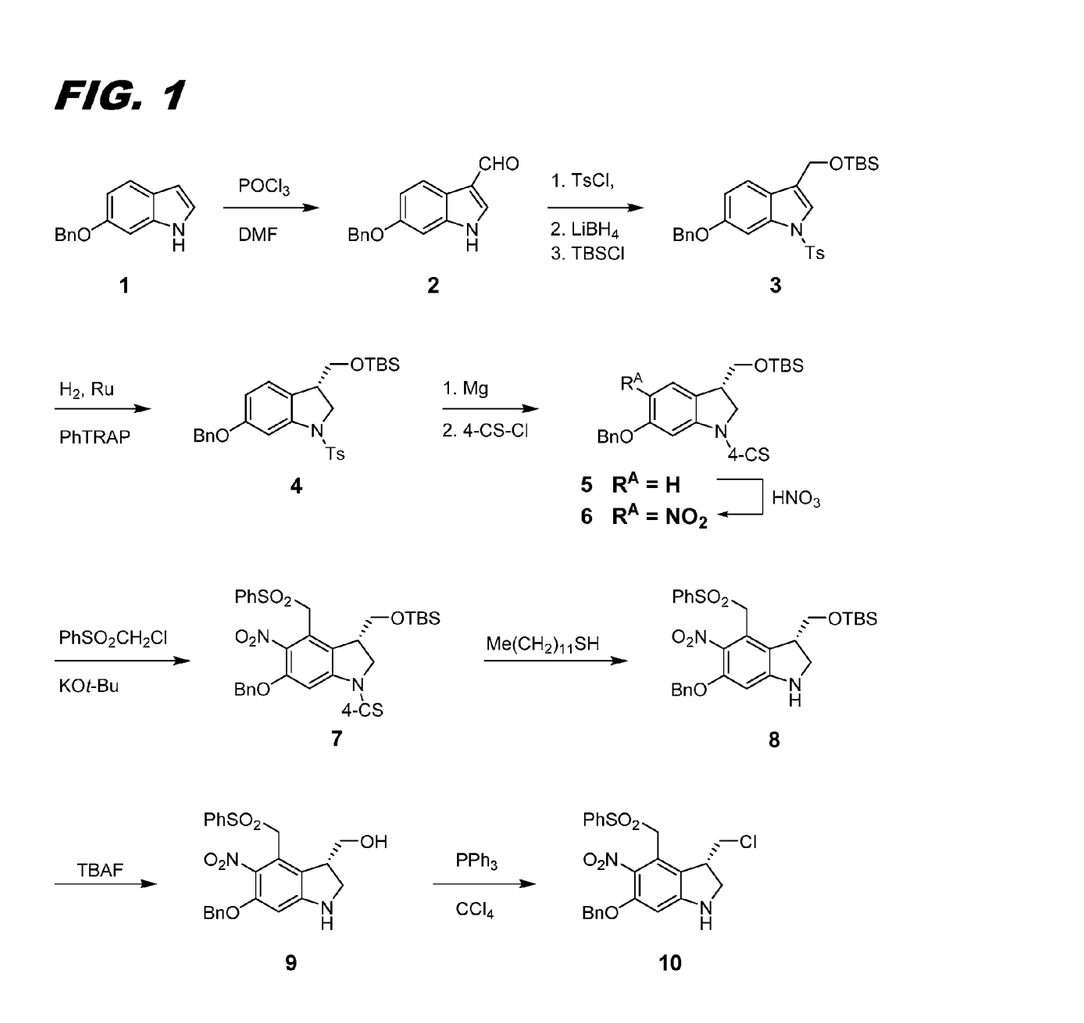
FIG. 1 shows a scheme for the synthesis of compounds according to formula (I) or (II).

Examples 1 through 9 relate to the synthesis of compounds shown in FIG. 1. Examples 10 through 14 relate to the synthesis of compounds shown in FIG. 2. Example 15 relates to the synthesis of compounds shown in FIG. 3.

Example 1

Indole Aldehyde 2

N,N-Dimethylformamide ("DMF," 75 mL) was added to a three-neck round bottomed flask equipped with a nitrogen inlet and thermocouple. The flask was cooled to an internal temperature of +2.8° C. with an ice water bath. Phosphorous (V) oxychloride (12.7 mL, 137.2 mmol, 1.25 equiv.) was added dropwise, keeping the internal temperature below 5° C. (~1 h). Once the addition was complete, 6-benzyloxyindole 1 (25.0 g, 109.7 mmol, 1.0 equiv.) was added in ~1 g portions, keeping the internal temperature below 5° C. (~1 h). The dark solution was warmed to room temperature ("RT") and held there for 1 h. A solution of sodium hydroxide (50 g) in water (250 mL) was prepared in a Morton flask and cooled to an internal temperature of 2.0° C. The dark reaction mixture was slowly added to the cold sodium hydroxide solution under vigorous stirring, keeping the internal temperature between 20-30° C. A light beige solid separated (final pH ~14). The slurry was heated slowly to an internal temperature of 70° C. and held for 10-15 min under a light nitrogen sweep to remove evolving dimethylamine, then heated to an internal temperature of 90° C. and held there for 15 min. Upon cooling to RT, the slurry was diluted with water (40 mL) and the solids were collected via filtration. The filter cake was washed with water (2×100 mL) and dried in a vacuum oven at 50° C. and 23 Hg pressure with a slight nitrogen sweep to constant weight, affording indole aldehyde 2 (27.3 g) as a beige/tan solid. The product was used without further purification and was ground to a fine powder, if clumpy, before use in the next step.

$^1$H NMR (400 MHz, DMSO-$d_6$) δ:11.94 (br, s), 9.87 (s, 1H), 8.15 (s, 1H), 7.96 (d, J=8.5 Hz, 1H), 7.47 (d, J=7.2 Hz, 2H), 7.40 (app t, J=7.4 Hz, 2H), 7.33 (t, J=7.0 Hz, 1H), 7.08 (s, 1H), 6.95 (d, J=8.5 Hz, 1H), 5.15 (s, 2H)

$^{13}$C NMR (101 MHz, DMSO-$d_6$) δ:184.7, 155.7, 137.9, 137.8, 137.2, 128.4, 127.7, 127.6, 121.4, 118.25, 118.23, 112.4, 96.9, 69.5

IR (KBr) (cm$^{-1}$):1634 (s), 1526 (m), 1426 (m), 1385 (m), 1159 (m)

HRMS (ESI) (m/z): Calc. for $C_{16}H_{13}NO_2$ [M+H]$^+$: 252.1019. Found: 252.1025.

Example 2

TBS Indole 3

To a Morton flask was added indole aldehyde 2 (50.00 g, 199.0 mmol, 1.00 equiv.), 4-dimethylaminopyridine ("DMAP," 1.22 g, 9.95 mmol, 0.05 equiv.) and dichloromethane ("DCM," 400 mL, 8 mL/g) to form a suspension. Triethylamine (42.0 mL, 298.4 mmol, 1.5 equiv.) was added followed by p-toluenesulfonyl chloride (42.15 g, 218.9 mmol, 1.10 equiv.). A remaining charge of DCM (100 mL) was used to wash any solids down the sides of the flask. The reaction mixture was vigorously stirred at room temperature for 1 h, after which it had become mostly homogeneous. The mixture was washed with a 1.0 N aqueous solution of hydrochloric acid (500 mL), then a saturated aqueous solution of brine (500 mL). The mixture was dried over sodium sulfate, filtered and concentrated in vacuo to afford the tosylated indole-aldehyde as a dark solid (84.06 g) that was used without further purification.

The tosylated indole aldehyde (84.06 g) was slurried in a mixture of 2-methyltetrahydrofuran (375 mL) and tetrahydrofuran ("THF," 125 mL) under nitrogen and was cooled to an internal temperature of 5° C. A solution of lithium borohydride (2.0 M in THF, 50.0 mL, 99.48 mmol, 0.50 equiv.) was added slowly, keeping the internal temperature below 10° C. (approx. 30 min). Once the addition was complete, the reaction mixture was warmed to RT and stirred for 30 min. The light slurry was cooled to an internal temperature of 5° C. and acetone (50 mL) was added slowly such that the internal temperature did not exceed 15° C. (approx. 20 min). The mixture was warmed to RT, stirred for 60 min, washed with a 1.0 M aqueous solution of a pH 7 sodium phosphate buffer (500 mL) and then saturated brine (250 mL). The organic layer was dried over sodium sulfate, filtered and concentrated in vacuo to afford the hydroxymethylindole as a dark red/brown viscous gel that was used without further purification.

The hydroxymethylindole and imidazole (20.32 g, 298.4 mmol, 1.5 equiv.) were dissolved in DMF (200 mL) with vigorous stirring. tert-Butyldimethylsilyl chloride ("TBS-Cl," 37.10 g, 238.8 mmol, 1.2 equiv.) was added followed by a remaining charge of DMF (50 mL), used to rinse down any solids down the sides of the flask. The reaction mixture was stirred for 60 min, then water (25 mL) was added slowly over 30 min. The mixture was seeded (250 mg), then aged for 60 min whereupon a thick bed of short rods formed. Water (225 mL) was added over 1 h to form a very thick slurry. Additional water (200 mL) was added to complete the desaturation of the product and lighten the slurry. The solids were collected by filtration, washed with water (2×200 mL) and the brown wet cake (120 g) was dried in a vacuum oven at 50° C. and 100 torr with a slight nitrogen sweep to constant weight. The dry cake (95.0 g) was further purified by flash column chromatography over silica gel (10 to 15% ethyl acetate in hexanes gradient) to afford the TBS indole 3 as a white solid (90.0 g, 86% over four steps from 6-benzyloxyindole).

M.p. (ethyl acetate/hexanes): 91-92° C.

$^1$H NMR (400 MHz, DMSO-$d_6$) δ: 7.67 (d, J=7.9 Hz, 2H), 7.40-7.52 (m, 7H), 7.38 (app t, J=6.6 Hz, 1H), 7.31 (d, J=7.8 Hz, 2H), 6.99 (d, J=8.7 Hz, 1H), 5.22 (s, 2H), 4.75 (s, 2H), 2.30 (s, 3H), 0.84 (s, 9H), 0.01 (s, 6H).

$^{13}$C NMR (101 MHz, DMSO-$d_6$) δ: 156.5, 145.3, 137.0, 135.7, 134.0, 130.1, 128.5, 127.8, 127.4, 126.5, 123.2, 123.1, 122.1, 120.9, 113.0, 98.8, 69.6, 57.1, 25.7, 21.0, 17.9, −5.4

IR (thin film) (cm$^{-1}$): 1619 (m), 1364 (s), 1170 (s), 1102 (s), 987 (m)

HRMS (ESI) (m/z): Calc. for $C_{29}H_{36}NO_4SSi$ [M+H]$^+$: 522.2129. Found: 522.2140.

Example 3

TBS Indoline 4

To two 350 mL stainless-steel autoclaves were charged indole 3 (30.0 g, 57.5 mmol, 1.00 equiv. in each). In a nitrogen filled glovebox, a dark orange stock solution of [Rh(cod)(acac)] (72.0 mg, 0.230 mmol, 0.002 equiv.) and (S,S)—(R,R)-PhTRAP (204 mg, 0.234 mmol, 0.002 equiv.) in dimethoxyethane (6.0 mL) was prepared by aging at RT for 20 min. The autoclave was brought into the glovebox and isopropanol (150 mL) was added to each autoclave, followed by 3 mL of the rhodium-catalyst solution. The autoclaves were then sealed under nitrogen, removed from glovebox and the atmosphere was replaced with hydrogen (purge, backfill five times). The autoclaves were pressurized with hydrogen to 750 psi, then heated 65° C. for 20 h, maintaining a hydrogen pressure of 750 psi. The atmosphere in the autoclaves was replaced with nitrogen (purge, backfill five times) at ambient pressure, cooled to RT, their contents combined and concentrated in vacuo. The crude product was passed through a plug of silica gel (0 to 15% ethyl acetate in hexanes gradient) to remove the catalyst and afford BS indoline 4 as a hard, white solid (57.63 g, 96%). The product was found to have an enantiomeric ratio of 99.1 favoring the (S) configuration as determined by chiral stationary phase HPLC (Sample preparation: 2 mg per mL methanol. Column: Phenomenex Lux Cellulose-4, 3 μm, 4.6×150 mm. Oven temperature: 25° C. Injection volume: 10 μL. Flow rate: 0.7 mL/min. Detector wavelength: 220 nm. Mobile phase: MeOH. Isocratic, hold for 8 minutes. Approximate retention times: 4.93 min (S), 5.65 min (R)). The absolute stereochemistry was determined by single X-ray crystallography.

M.p. (ethyl acetate/hexanes): 78-79° C.

$[α]_D^{22}$: +40.1° (c=10.0 mg/mL, toluene)

$^1$H NMR (400 MHz, DMSO-$d_6$) δ: 7.56 (d, J=8.1 Hz, 2H), 7.49-7.44 (m, 2H), 7.41 (app t, J=7.4 Hz, 2H), 7.33-7.37 (m, 1H) 7.31 (d, J=8.1 Hz, 2H), 7.13, (d, J=1.7 Hz, 1H), 7.08 (d, J=8.2 Hz, 1H), 6.65 (dd, J=8.3, 2.1 Hz, 1H), 5.13 (s, 2H), 3.90 (dd, J=10.7, 8.8 Hz, 1H), 3.69 (dd, J=10.8, 4.3 Hz, 1H), 3.30-3.38 (m, 1H), 3.17-3.26 (m, 2H), 2.32 (s, 3H), 0.78 (s, 9H), −0.08 (s, 3H), −0.12 (s, 3H)

$^{13}$C NMR (101 MHz, DMSO-$d_6$) δ: 158.5, 144.2, 142.6, 137.0, 133.0, 129.8, 128.4, 127.7, 127.4, 127.0, 125.9, 124.6, 110.0, 101.3, 69.3, 64.7, 52.9, 41.3, 25.6, 20.9, 17.8, −5.6, −5.8

IR (thin film) (cm$^{-1}$): 1614 (m), 1500 (m), 1349 (s), 1160 (s), 1096 (s)

HRMS (ESI) (m/z): Calc. for $C_{29}H_{38}NO_4SSi$ [M+H]$^+$: 524.2285. Found: 524.2295.

Example 4

Cyanobenzenesulfonyl Indoline 5

A three-neck round bottomed flask was equipped with a nitrogen inlet, thermocouple and an outlet vent. The flask was charged with compound 4 (50.00 g, 95.46 mmol, 1.00 equiv.) and a mixture of toluene (250 mL) and methanol (250 mL) was added. The solution was sparged with nitrogen for approximately 10 min at RT, then kept under a small nitrogen sweep. Magnesium turnings (2.32 g, 95.46 mmol, 1.00 equiv.) were added and the mixture stirred for 1 h whereupon an exotherm and off-gassing were noted. The internal temperature was maintained below 35° C. with an ice-water bath. Additional magnesium was added, 1.00 equiv. at a time, at approximately 1 h intervals, then the mixture was held overnight (or until all the solid magnesium reacted). The slurry was poured into a cold (0-5° C.) biphasic solution of toluene (500 mL) and 10 wt % urea in 3 N aqueous HCl (1.00 L) and vigorously agitated. The pH of the aqueous layer should be <1. The layers were separated, and any rag layer (predominately toluenesulfinate salts) was discarded with the aqueous layer. The organic layer was washed with a 1.0 M aqueous solution of a pH 7 sodium phosphate buffer (375 mL), ensuring the pH of the aqueous layer was >6. The organic layer was dried over sodium sulfate, filtered and concentrated in vacuo to afford the deprotected indoline as dark brown solid (37.81 g). (Caution: This reaction produces hydrogen gas and should be performed in a well-ventilated hood.)

The crude indoline was dissolved in ethyl acetate (500 mL) and cooled to an internal temperature of 0-5° C. N,N-Diisopropylethylamine ("DIPEA," 20.0 mL, 114.54 mmol, 1.20 equiv.) was added followed by recrystallized 4-cyanobenzenesulfonyl chloride ("4-CS—Cl," 20.63 g, 100.23 mmol, 1.05 equiv.). A white precipitate formed over 15-20 min and the slurry was warmed to RT. The reaction mixture was stirred for 1 h, was washed with a 10 wt % aqueous solution of citric acid (250 mL), then was washed with a 1.0 M aqueous solution of a pH 7 sodium phosphate buffer (375 mL), ensuring the pH of the aqueous layer was >6. The red-orange stream was stirred over sodium sulfate and activated carbon (DARCO® G-60, 100 mesh, 25.0 g) for two hours, then was filtered over CELITE™ (3.5" dia, 0.75" ht), rinsing the pad with ethyl acetate (2×25 mL). The light orange solution was concentrated in vacuo to afford a thick orange oil (55.27 g). To the oil was added isopropanol (500 mL) and the solvent level was marked. Additional isopropanol (500 mL) is added followed by dimethylethylamine (0.500 mL) and the oil is dissolved with mild heating at an internal temperature of ~35° C., then was allowed to cool to room temperature under mechanical stirring. The solution was seeded (250 mg) and the mixture was stirred for 15 h. The slurry was concentrated slowly (on this scale, 45 min to 1 h, vacuum pressure <70 torr, bath temperature no greater than 35° C.) to the 10 mL/g marked line. The thick slurry was mechanically stirred for 1 h, then water (500 mL) containing dimethylethylamine (0.500 mL) was added slowly over 1 h. The pH was checked, and if <7, additional dimethylethylamine was added in 0.01 mL/g increments, and the mixture was aged for an additional 1 h. The solids were collected by filtration, washed with 50 v % aqueous isopropanol (2×250 mL) and the wet cake was dried in a vacuum oven at 50° C. and 100 torr with a slight nitrogen sweep to constant weight to afford cyanonbenzenesulfonyl indoline 5 as small, beige to pink-colored needles (42.91 g, 84% over two steps).

M.p. (isopropanol/water): 77-78° C.

$^1$H NMR (400 MHz, DMSO-$d_6$) δ: 8.03 (d, J=8.6 Hz, 2H), 7.86 (d, J=8.3 Hz, 2H), 7.39-7.49 (m, 4H), 7.33-7.39 (m, 1H), 7.08-7.15 (m 2H), 6.69 (dd, J=8.2, 2.4 Hz, 2H), 5.15 (s, 2H), 3.98 (dd, J=10.7, 9.2 Hz, 1H), 3.71 (dd, J=10.9, 4.8 Hz, 1H), 3.38-3.30 (m, 2H), 3.21-3.29 (m, 1H). 0.75 (s, 9H), −0.08 (s, 3H), −0.14 (s, 3H)

$^{13}$C NMR (101 MHz, DMSO-$d_6$) δ: 158.6, 141.9, 139.8, 137.0, 133.6, 128.4, 127.8, 127.7, 127.4, 126.1, 124.7, 117.3, 116.2, 110.6, 101.1, 69.4, 64.5, 52.9, 41.2, 25.6, 17.8, −5.6, −5.8.

Example 5

Nitro Indoline 6

To a solution of cyanobenzenesulfonyl indoline 5 (333 mg, 1.00 equiv.) in DCM (3.32 mL) was added fuming nitric acid (34 μL, 1.25 equiv.). After 30 min an additional charge of fuming nitric acid (34 μL, 1.25 equiv.) was added. After 20 min, the solution was diluted with DCM (10 mL) and washed with an aqueous solution of a sodium phosphate buffer (1 M, pH=7, 10 mL). The aqueous layer was extracted with DCM and the combined organic phases were dried over sodium sulfate, filtered and concentrated in vacuo to afford a brown solid. The solid was purified by flash column chromatography over silica gel (0 to 25% EtOAc in hexanes gradient) to afford the nitro indoline 6 (261 mg, 72%) as a yellow foam.

$^1$H NMR (400 MHz, DMSO-$d_6$) δ: 8.03 (d, J=8.0 Hz, 2H), 7.84-7.90 (m, 3H), 7.45-7.51 (m, 4H), 7.38-7.43 (m, 1H), 7.34 (s, 1H), 5.44 (s, 2H), 4.05-4.10 (m, 1H), 3.75 (dd, J=10.5, 4.7 Hz, 1H), 3.54 (q, J=4.5 Hz, 1H), 3.34-3.42 (m, 2H), 0.69 (m, 9H), −0.10 (s, 3H), −0.19 (s, 3H).

Example 6

Phenylsulfonylmethyl Indoline 7

To a solution of nitro indoline 6 (261 mg) in THF (1.3 mL) was added chloromethylphenyl sulfone (97.3 mg, 1.10 equiv.). The solution was cooled to an internal temperature of −27° C. and a solution of potassium tert-butoxide in THF (990 μL, 2.20 equiv.) was added in one portion, causing the internal temperature to rise to −20.8° C. and the solution to become deep red. The mixture was warmed to −3.1° C. and held for 30 min before being quenched with acetic acid (77.4 μL, 3.00 equiv.). The slurry was dissolved in DCM (10 mL), washed with an aqueous solution of a sodium phosphate buffer (1 M, pH=7, 10 mL), dried over sodium sulfate, filtered and concentrated in vacuo to afford a brown gel. The residue was purified by flash column chromatography over silica gel (0 to 40% EtOAc in hexanes gradient) to afford phenylsulfonylmethyl indoline 7 as a hard, dark yellow foam (247.6 mg, 75%).

$^1$H NMR (400 MHz, DMSO-$d_6$) δ: 8.11 (d, J=8.3 Hz, 2H), 7.86 (d, J=8.6 Hz, 2H), 7.63-7.67 (m, 1H), 7.56-7.58 (m, 2H), 7.38-7.51 (m, 8H), 5.46 (d, J=12.8 Hz, 1H), 5.40 (d, J=12.9 Hz, 1H), 4.84 (d, J=14.7 Hz, 1H), 4.59 (d, J=14.4 Hz, 1H), 3.80 (d, J=10.6 Hz, 1H), 3.30-3.36 (m, 2H), 3.01 (dd, J=9.9, 7.8 Hz, 1H), 2.87 (app q, J=6.8 Hz, 1H), 0.69 (s, 9H), −0.17 (s, 3H), −0.25 (s, 3H).

Example 7

Compound 8

A solution of compound 7 (100 mg) in DMF (1.00 mL) and 1-dodecanethiol (294 μL, 9.0 equiv.) was degassed by nitrogen sparging for 10 min. Cesium carbonate (377 mg, 8.5 equiv.) was added and the mixture was stirred for 45 min before being partitioned between ethyl acetate (15 mL) and a 10 wt % aqueous citric acid solution (20 mL). The layers were separated and the aqueous layer was extracted with ethyl acetate (10 mL) and the combined organic layers were washed with brine (10 mL), dried over sodium sulfate, filtered and concentrated in vacuo to afford a yellow oil. The oil was purified by flash column chromatography over silica gel (0 to 75% EtOAc in hexanes gradient) to afford compound 8 as a yellow foam (72.7 mg, 94%).

$^1$H NMR (400 MHz, DMSO-$d_6$) δ: 7.76-7.80 (m, 1H), 7.68-7.71 (m, 2H), 7.61-7.65 (m, 2H), 7.39-7.43 (m, 4H), 7.31-7.37 (m, 1H), 6.67 (br s, 1H), 6.33 (s, 1H), 5.20 (d, J=12.4 Hz, 1H), 5.14 (d, J=12.4 Hz, 1H), 4.87 (d, J=14.4 Hz, 1H), 4.82 (d, J=14.4 Hz, 1H), 3.45 (d, J=7.6 Hz, 2H), 3.11-3.21 (m, 2H), 2.78 (q, J=7.5 Hz, 1H), 0.78 (s, 9H), −0.06 (s, 3H), −0.08 (s, 3H).

Example 8

Hydroxymethyl Indoline 9

Compound 8 can be converted to hydroxymethyl indoline 9 using tetrabutylammonium fluoride ("TBAF), generally following conditions described hereinbelow.

Example 9

Chloromethyl Indoline 10

Hydroxymethyl indoline 9 can be converted to chloromethyl indoline 10 using triphenylphosphine and carbon tetrachloride, as described in Fukuda et al. 1997c.

Example 10

Compound 12

5,6,7-Trimethyoxy-1H-indole-2-carboxylic acid (CAS Reg. No. 128781-07-7, 500 mg), DMF (7.4 µL, 0.05 equiv.) and THF (5.00 mL) were stirred until a homogeneous solution formed (~2 min). Oxalyl chloride (326 µL, 2.00 equiv.) was added and vigorous gas evolution was observed. After stirring for 30 min, the yellow solution was concentrated in vacuo, then down from heptane to afford a yellow solid. MTBE (10 mL) was added, and the mixture was heated whereupon a brown oil separated. The yellow supernatant was filtered through a syringe filter and heptane was added and the mixture was concentrated in vacuo to afford a yellow solid. The solid was slurried in heptane (5 mL) then filtered to afford acid chloride 11 as a yellow solid (473 mg, 93%).

$^1$H NMR (400 MHz, $C_6D_6$) δ:8.46 (br s, 1H), 7.22 (d, J=2.3 Hz, 1H), 6.40 (s, 1H), 3.70 (s, 3H), 3.60 (s, 3H), 3.36 (s, 3H).

Compound 8 (109.6 mg) was dissolved in DCM (1.10 mL) and 2,6-lutidine (45 µL, 2.0 equiv.) was added. Acid chloride 11 (57 mg, 1.10 equiv.) was added and the initially orange solution became light yellow. After 30 min, the mixture was diluted with DCM (10 mL), then washed with a saturated, aqueous sodium bicarbonate (5 mL), then a 10 wt % aqueous citric acid (5 mL). The organic layer was dried over sodium sulfate, filtered and concentrated in vacuo to afford a crude residue. The residue was purified by flash column chromatography over silica gel (0 to 100% EtOAc in hexanes gradient) to afford compound 12 as a yellow solid (137.1 mg, 89%).

$^1$H NMR (400 MHz, DMSO-$d_6$) δ:11.58 (d, J=1.5 Hz, 1H), 8.15 (br s, 1H), 7.81-7.85 (m, 1H), 7.76-7.78 (m, 2H), 7.67-7.71 (m, 2H), 7.39-7.44 (m, 4H), 7.33-7.37 (m 1H), 7.06 (d, J=2.0 Hz, 1H), 6.93 (s, 1H), 5.28 (d, J=12.4 Hz, 1H), 5.22 (d, J=12.1 Hz, 1H), 5.02 (d, J=14.6 Hz, 1H), 4.71 (d, J=14.4 Hz, 1H), 4.20-4.28 (m, 2H), 3.91 (s, 3H), 3.81 (s, 3H), 3.79 (s, 3H), 3.66 (dd, J=10.4, 5.3 Hz, 1H), 3.56 (dd, J=10.4, 6.6 Hz, 1H), 3.13-3.19 (m, 1H), 0.67 (s, 9H), −0.15 (s, 3H), −0.22 (s, 3H).

Example 11

Compound 13

To a solution of compound 12 (137 mg) in acetonitrile (1.37 mL) was added zinc dust (112 mg, 10.0 equiv.) and acetic acid (97.9 µL, 10.0 equiv.). The mixture was stirred for 72 h, then was filtered. The cake was washed with ethyl acetate (2×5 mL). The combined organic phases were washed with aqueous sodium phosphate buffer (1 M, pH=7), dried over sodium sulfate, filtered and concentrated in vacuo to afford a clear oil. The residue was purified by flash column chromatography over silica gel (0 to 50% EtOAc in hexanes gradient) to afford compound 13 as a light yellow foam (94.2 mg, 72%).

$^1$H NMR (400 MHz, DMSO-$d_6$) δ:11.33 (s, 1H), 7.75-8.06 (m 4H), 7.61-7.70 (m, 2H), 7.37-7.53 (m, 4H), 7.30-7.36 (m, 1H), 6.85-6.94 (m, 2H), 5.10 (br s, 2H), 4.81 (d, J=14.4 Hz, 1H), 4.60-4.74 (m, 3H), 4.11-4.19 (m, 1H), 4.03-4.11 (m, 1H), 3.90 (s, 3H), 3.80 (s, 3H), 3.78 (s, 3H), 3.47-3.56 (m, 1H), 3.39-3.47 (m, 1H), 3.04 (q, J=6.7 Hz, 1H), 0.69 (s, 9H), −0.13 (s, 3H), −0.17 (s, 3H).

Example 12

Compound 15

To a solution of compound 10 (94.7 mg) in DCM (950 µL) was added magnesium sulfate (44.3 mg, 3.00 equiv.) and methyl 2-hydroxy-2-methoxyacetate 14 (25.8 µL, 2.00 equiv.). The mixture was stirred for 23 h, then the salts were filtered off and the cake washed with DCM (2×5 mL). The solution was concentrated in vacuo and the crude product was used directly in the next step.

The crude product from the preceding paragraph was dissolved in dimethyl sulfoxide (950 µL) and cesium carbonate (200 mg, 5.00 equiv.) was added. The slurry was heated at 50° C. for 4 h, then was cooled to RT and poured into a 10 wt % citric acid in saturated aqueous brine (25 mL). The mixture was extracted with ethyl acetate (2×15 mL), and the combined organic extracts were washed with a half-saturated solution of brine (2×20 mL). The organic layer was dried over sodium sulfate, filtered and concentrated in vacuo to afford an orange oil. The oil was purified by flash column chromatography over silica gel (0 to 50% EtOAc in hexanes gradient) to afford product 15 as a yellow semisolid (66.3 mg, 77%).

$^1$H NMR (400 MHz, DMSO-$d_6$) δ: 12.10 (s, 1H), 11.36 (s, 1H), 8.04 (br s, 1H), 7.60 (br s, 2H), 7.40 (app t, J=7.3 Hz, 2H), 7.32 (app t, J=7.3 Hz, 1H), 7.21 (d, J=1.5 Hz, 1H), 6.96 (br s, 1H), 6.93 (s, 1H), 5.24 (br s, 2H), 4.59 (m, 1H), 4.32 (br d, J=9.6 Hz, 1H), 3.91 (s, 3H), 3.87 (m, 4H), 3.81 (s, 3H), 3.78 (s, 3H), 3.73-3.76 (m, 2H), 0.75 (s, 9H), −0.07 (s, 3H), −0.16 (s, 3H).

Example 13

Compound 16

To a slurry of compound 15 (218.9 mg) in methanol (2.20 mL) was added ammonium formate (101 mg, 5.00 equiv.).

The system was purged with nitrogen, then 20 wt % palladium hydroxide on carbon (50% water wet, 11.0 mg, 0.025 equiv) was added and the system was placed under nitrogen. The mixture was heated to 50° C. whereupon product crystallized out of solution, then cooled to room temperature. THF (5.00 mL) was added and the mixture was filtered over CELITE™ and the cake was washed with THF (3×3 mL). The combined organic layers were concentrated in vacuo to afford a yellow solid. The yellow solid was diluted with water (5 mL) and was extracted with ethyl acetate (2×10 mL). The combined organic layers were washed with a saturated brine (10 mL), dried over sodium sulfate, filtered and concentrated in vacuo to afford a yellow foam that was used in the next step without further purification.

The foam was dissolved in THF (1.60 mL) and a solution of TBAF in THF (1.0 M, 470 µL, 1.50 equiv.) was added and the mixture was heated to 35° C. under nitrogen for 3 h. The solution was cooled to room temperature and quenched with acetic acid (31.4 µL, 1.75 equiv.), diluted with ethyl acetate (10 mL), then washed with a saturated aqueous solution of brine (2×10 mL). The organic layer was dried over sodium sulfate, filtered and concentrated in vacuo to afford a dark yellow gel. The yellow gel was triturated from methanol (3 mL) twice to afford compound 16 as a light tan solid (94.3 mg, 61%).

$^1$H NMR (400 MHz, DMSO-$d_6$) δ: 11.53 (s, 1H), 11.31 (s, 1H), 9.67 (s, 1H), 7.76 (br s, 1H), 7.13 (d, J=1.5 Hz, 1H), 6.98 (d, J=1.8 Hz, 1H), 6.94 (s, 1H), 4.93 (t, J=5.3 Hz, 1H), (4.56 (br t, J=9.9 Hz, 1H), 4.34 (dd, J=10.7, 3.9 Hz, 1H), 3.92 (s, 3H), 3.86 (s, 3H), 3.81 (s, 3H), 3.79 (s, 3H), 3.74-3.78 (m, 1H), 3.67 (tt, J=8.2, 4.3 Hz, 1H), 3.46 (ddd, J=10.2, 7.5, 5.6 Hz, 1H).

Example 14

Duocarmycin SA

To a yellow slurry of compound 12 (84.1 mg) and 1,1'-(azodicarbonyl)dipiperdine ("ADDP," 65 mg, 1.50 equiv.) in THF (1.26 mL) was added PBu$_3$ (65 µL, 1.50 equiv.) under nitrogen. The suspension darkened immediately, became homogenous, and a thick precipitate formed. After 20 min, the mixture was diluted with DCM (500 µL) and directly purified by flash column chromatography over silica gel (50 to 100% EtOAc in hexanes gradient) to afford a light yellow solid. The solid was washed with MTBE (2×2 mL) then dried to afford 49.1 mg of an off-white solid. Spectral characteristics of the solid matched those for duocarmycin SA (Fukuyama et al. 2003).

$^1$H NMR (400 MHz, CDCl$_3$) δ:9.88 (br s, 1H), 9.30 (br s, 1H), 7.03 (s, 1H), 6.95 (d, J=2.3 Hz, 1H), 6.79 (s, 1H), 6.61 (d, J=2.0 Hz, 1H), 4.48 (dd, J=10.5, 4.9 Hz, 1H), 4.40 (d, J=10.6 Hz, 1H), 4.08 (s, 3H), 3.94 (s, 3H), 3.91 (s, 3H), 3.90 (s, 3H), 2.79 (dt, J=7.6, 4.8 Hz, 1H), 1.76 (dd, J=7.6, 4.6, 1H), 1.58 (t, J=4.7 Hz, 1H).

$^{13}$C NMR (101 MHz, CDCl$_3$) δ:177.8, 161.5, 161.1, 160.9, 150.4, 141.0, 138.8, 131.6, 129.8, 128.4, 126.7, 126.3, 123.2, 112.5, 107.7, 107.5, 97.6, 61.5, 61.1, 56.2, 54.8, 52.1, 31.3, 26.0, 23.5.

LCMS (m/z): Calc. for $C_{25}H_{24}N_3O_7$ [M+H]$^+$: 478. Found: 478.

Example 15

Seco-Duocarmycin SA 18

Figure 2:
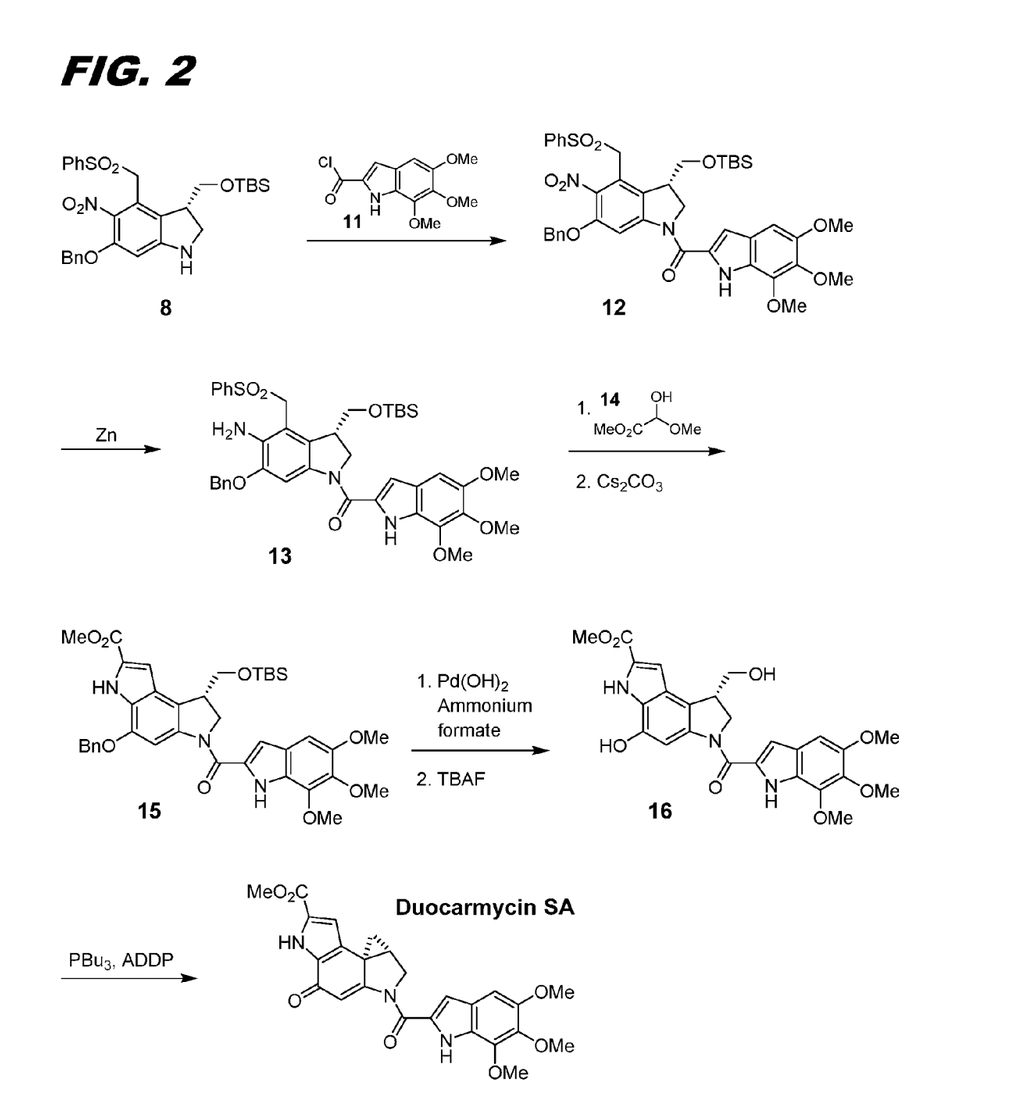
FIG. 2 shows a scheme for the synthesis of an MGBA having a CPI alkylating subunit (duocarmycin SA), using a compound of this invention.
Figure 3:
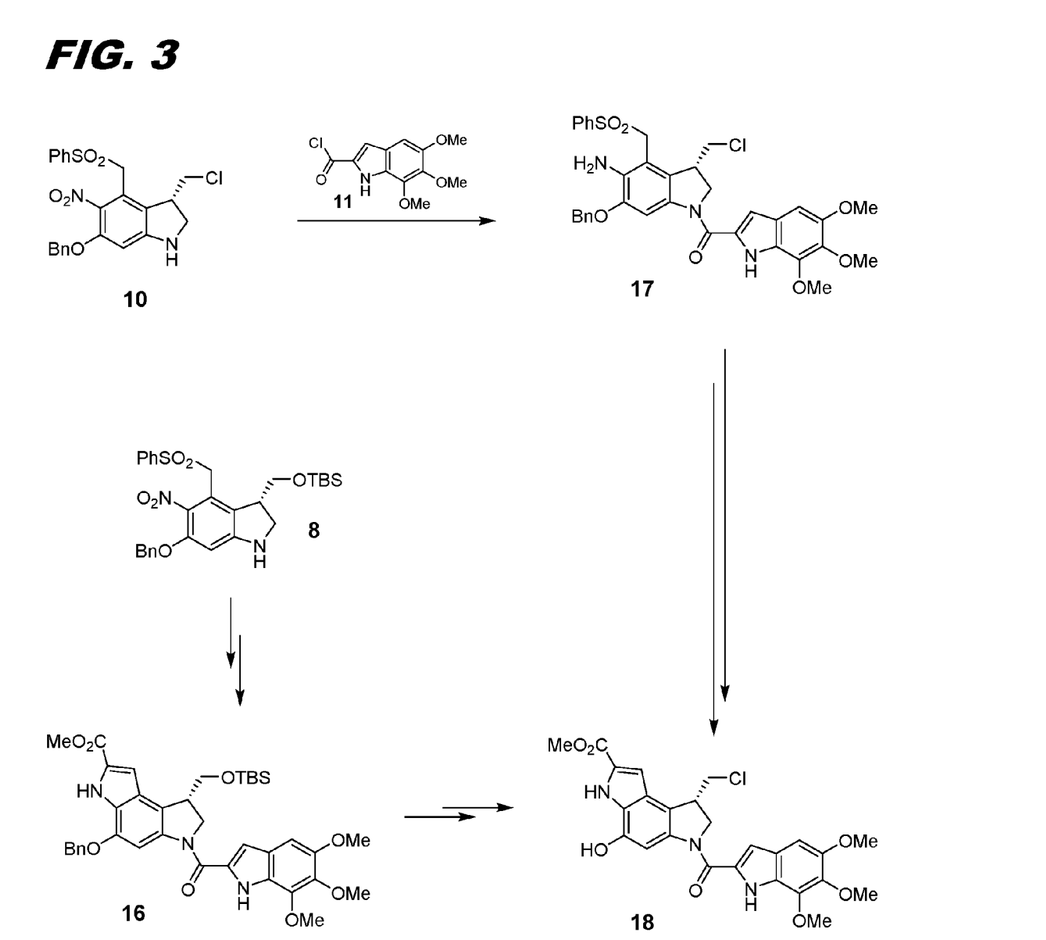
FIG. 3 shows a scheme for the synthesis of an MGBA having a seco-CPI alkylating subunit, using compounds of this invention.

Seco-Duocarmycin SA 18 can be prepared from compound 8 via compound 15 (see FIG. 2). Compound 15 can be converted to compound 18 by removal of the TBS group to give the corresponding hydroxylmethyl compound with TBAF, conversion of the hydroxymethyl group to a chloromethyl group with triphenylphosphine/carbon tetrachloride, and reductive removal of the benzyl group, generally following the procedure for analogous reactions described hereinabove.

Alternatively, compound 10 can be coupled with acid chloride 11, which can then be converted to seco-duocarmycin SA 18 by cyclization to form the left-side pyrrole group, generally using reagents for analogous reactions described hereinabove and generally following the conditions for them.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Boger et al., J. Am. Chem. Soc. 1988, 110, 1321.
Boger et al., J. Am. Chem. Soc. 1993, 115, 9025.
Boger, U.S. Pat. No. 6,281,354 B1 (2001).
Boger and Johnson, Proc. Nat. Acad. Sci. (USA) 1995, 92, 3642.
Boger et al., Chem. Rev. 1997, 97, 787 (1997a).
Boger et al., J. Am. Chem. Soc. 1997, 119, 4987 (1997b).
Boger et al., J. Org. Chem. 2000, 65, 4101.
Boyle et al., Bioorg. Med. Chem. Lett. 2010, 20, 1854.
Choi et al., Bull. Korean Chem. Soc. 2009, 30 (11), 2815.
Fukuda et al., Tetrahedron 1994, 50 (9), 2793.
Fukuda et al., Bioorg. Med. Chem. Lett. 1997, 7 (13), 1683 (1997a).
Fukuda et al., Heterocycles 1997, 48 (12), 2303 (1997b).
Fukuda et al., Tetrahedron Lett. 1997, 38 (41), 7207 (1997c).
Fukuyama et al., J. Am. Chem. Soc. 2003, 125, 6630.
Hiroya et al., Org. Lett. 2004, 6 (17), 2953.
Hurley et al., Science 1984, 226, 843.
Kinugawa et al., Org. Proc. Res. Dev. 1998, 2, 344.
Kobayashi et al., Cancer Res. 1994, 54, 2404.
Kraus et al., J. Org. Chem. 1985, 50, 284.
Kuwano et al., Org. Lett. 2004, 6 (13), 2213.
Lajiness et al., J. Med. Chem. 2010, 53, 7731.
Li et al., Cancer Res. 1992, 52, 4904.
Muratake et al., Tetrahedron Lett. 1994, 35 (16), 2573.
Muratake et al., Chem. Pharm. Bull. 1995, 43 (6), 1064.

Muratake et al., *Chem. Pharm. Bull.* 1998, 46 (3), 400 (1998a).

Muratake et al., *Chem. Pharm. Bull.* 1998, 46 (4), 559 (1998b).

Muratake et al., *Chem. Pharm. Bull.* 2000, 48 (10), 1558.

Sakamoto et al., *J. Chem. Soc.* (*Perkin Trans.* 1) 1993, 1941.

Sufi et al., U.S. Pat. No. 8,461,117 B2 (2013).

Tichenor et al., *J. Am. Chem. Soc.* 2006, 128, 15683.

Tichenor et al., *J. Am. Chem. Soc.* 2007, 129, 10858.

Tietze et al., *ChemBioChem* 2001, 2, 758.

Yamada et al., *J. Am. Chem. Soc.* 2003, 125, 6630.

Zhang et al., U.S. Pat. No. 8,852,599 B2 (2014).

What is claimed is:

1. A compound of the structure according to formula (I)

(I)

wherein $R^1$ is $CH_2$(phenyl) wherein the phenyl group is optionally substituted with one or more of Br, Cl, F, $C_1$-$C_3$ alkyl, O($C_1$-$C_3$ alkyl), CN, $NH_2$, NH($C_1$-$C_3$)alkyl, N($C_1$-$C_3$ alkyl)$_2$, or $CF_3$; $CH_2$(naphthyl) wherein the naphthyl group is optionally substituted with one or more of Br, Cl, F, $C_1$-$C_3$ alkyl, O($C_1$-$C_3$ alkyl), CN, $NH_2$, NH($C_1$-$C_3$)alkyl, N($C_1$-$C_3$ alkyl)$_2$, or $CF_3$; trimethyl silyl; triethyl silyl; triisopropyl silyl; t-butyldiphenyl silyl; triphenylsilyl; or t-butyldimethyl silyl;

$R^2$ is an aromatic group selected from phenyl, naphthyl, pyridyl, pyrimidinyl, imidazolyl, and pyrazolyl, the aromatic group being optionally substituted with one or more of Br, Cl, F, $C_1$-$C_3$ alkyl, O($C_1$-$C_3$ alkyl), CN, $NH_2$, NH($C_1$-$C_3$)alkyl, N($C_1$-$C_3$ alkyl)$_2$, or $CF_3$;

and $R^3$ is trimethyl silyl, triethyl silyl, triisopropyl silyl, t-butyldiphenyl silyl, triphenylsilyl, or t-butyldimethyl silyl;

or a salt thereof.

2. A compound according to claim 1, wherein $R^1$ is benzyl.

3. A compound according to claim 1, wherein $R^2$ is phenyl.

4. A compound according to claim 1, wherein $R^3$ is t-butydimethylsilyl.

5. A compound according to claim 1, of the structure according to formula (Ia):

(Ia)

6. A compound of the structure according to formula (II)

(II)

wherein $R^1$ is $CH_2$(phenyl) wherein the phenyl group is optionally substituted with one or more of Br, Cl, F, $C_1$-$C_3$ alkyl, O($C_1$-$C_3$ alkyl), CN, $NH_2$, NH($C_1$-$C_3$)alkyl, N($C_1$-$C_3$ alkyl)$_2$, or $CF_3$; $CH_2$(naphthyl) wherein the naphthyl group is optionally substituted with one or more of Br, Cl, F, $C_1$-$C_3$ alkyl, O($C_1$-$C_3$ alkyl), CN, $NH_2$, NH($C_1$-$C_3$)alkyl, N($C_1$-$C_3$ alkyl)$_2$, or $CF_3$; trimethyl silyl; triethyl silyl; triisopropyl silyl; t-butyldiphenyl silyl; triphenylsilyl; or t-butyldimethyl silyl;

and

$R^2$ is an aromatic group selected from phenyl, naphthyl, pyridyl, pyrimidinyl, imidazolyl, and pyrazolyl, the aromatic group being optionally substituted with one or more of Br, Cl, F, $C_1$-$C_3$ alkyl, O($C_1$-$C_3$ alkyl), CN, $NH_2$, NH($C_1$-$C_3$)alkyl, N($C_1$-$C_3$ alkyl)$_2$, or $CF_3$;

or a salt thereof.

7. A compound according to claim 6, wherein $R^1$ is benzyl.

8. A compound according to claim 6, wherein $R^2$ is phenyl.

9. A compound according to claim 6, of the structure according to formula (IIa):

(IIa)

* * * * *